US010977292B2

(12) United States Patent
Eifert et al.

(10) Patent No.: US 10,977,292 B2
(45) Date of Patent: Apr. 13, 2021

(54) PROCESSING DOCUMENTS IN CONTENT REPOSITORIES TO GENERATE PERSONALIZED TREATMENT GUIDELINES

(71) Applicant: International Business Machines Corporation, Armonk, NY (US)

(72) Inventors: Cheryl L. Eifert, Watertown, MA (US); Claudia S. Huettner, Jamaica Plain, MA (US); Marta Sanchez-Martin, Somerville, MA (US); Vanessa Michelini, Boca Raton, FL (US); Kirk Beaty, Goldens Bridge, NY (US); Jia Xu, Somerville, MA (US); Fang Wang, Plano, TX (US); Pengwei Yang, Belmont, MA (US); Bhuvan Sharma, Belmont, MA (US); Mengdi Zhu, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 162 days.

(21) Appl. No.: 16/247,722

(22) Filed: Jan. 15, 2019

(65) Prior Publication Data
US 2020/0226164 A1 Jul. 16, 2020

(51) Int. Cl.
*G06F 16/00* (2019.01)
*G06F 16/35* (2019.01)
(Continued)

(52) U.S. Cl.
CPC .......... *G06F 16/353* (2019.01); *G06F 16/334* (2019.01); *G06F 16/3334* (2019.01);
(Continued)

(58) Field of Classification Search
CPC .. G06F 16/3334; G06F 16/334; G06F 16/353; G06F 16/335; G06F 16/24578;
(Continued)

(56) References Cited

U.S. PATENT DOCUMENTS 7,130,848 B2   10/2006   Oosta
7,461,006 B2   12/2008   Gogolak
(Continued)

FOREIGN PATENT DOCUMENTS

WO   2016016879 A1   2/2016
WO   2019243486 A1   12/2019

OTHER PUBLICATIONS

Wei et al., "tmVar: a text mining approach for extracting sequence variants in biomedical literature", Original Paper, BIOINFORMATICS, vol. 29, No. 11, Apr. 5, 2013, https://academic.oup.com/bioinformatics/article/29/11/1433/220291, 7 pages.

(Continued)

*Primary Examiner* — Anh Ly
(74) *Attorney, Agent, or Firm* — Ryan Lewis; Edell, Shapiro & Finnan, LLC

(57) ABSTRACT

A computer system processes documents in a content repository. Each document of a plurality of documents is classified into one of a functional category and a clinical category. Each document is annotated using one or more corpora to generate document annotations. Documents satisfying one or more query terms are identified by comparing each query term to the document annotations. The identified documents are ranked based on a determined relevance. Guidelines are produced based on the ranking of the identified documents. Embodiments of the present invention further include a method and program product for processing documents in a content repository in substantially the same manner described above.

15 Claims, 12 Drawing Sheets

(51) Int. Cl.
  *G06F 16/33* (2019.01)
  *G06N 3/02* (2006.01)
  *G16H 20/00* (2018.01)
  *G06F 40/169* (2020.01)
(52) U.S. Cl.
  CPC ............. *G06F 40/169* (2020.01); *G06N 3/02* (2013.01); *G16H 20/00* (2018.01)
(58) Field of Classification Search
  CPC ...... G06F 16/285; G06F 16/93; G06F 17/241; G06F 16/35; G06F 16/33; G06F 17/24; G06F 19/324; G06F 19/322; G06F 19/326; G06F 19/321; G06F 40/169; G06F 16/1744; G06F 16/22; G06F 16/2272; G06F 16/245; G06F 16/174; G06F 16/00; G06F 17/30; G06N 3/02; G16H 10/60; G16H 40/20; G16H 50/70; G16H 70/00
  See application file for complete search history.

(56) References Cited

U.S. PATENT DOCUMENTS

| | | | |
|---|---|---|---|
| 8,903,825 | B2 | 12/2014 | Parker et al. |
| 9,483,532 | B1 | 11/2016 | Zhang et al. |
| 9,495,349 | B2 | 11/2016 | Angell et al. |
| 9,690,861 | B2 | 6/2017 | Boloor et al. |
| 10,713,440 | B2* | 7/2020 | Pestian ............... G06F 16/3344 |
| 2001/0034023 | A1 | 10/2001 | Stanton et al. |
| 2003/0177112 | A1 | 9/2003 | Gardner |
| 2004/0142325 | A1 | 7/2004 | Mintz et al. |
| 2005/0060305 | A1 | 3/2005 | Hopkins |
| 2007/0112748 | A1 | 5/2007 | Angell et al. |
| 2008/0027913 | A1* | 1/2008 | Chang ..................... G06F 16/00 |
| 2009/0012956 | A1 | 1/2009 | Wen et al. |
| 2009/0019032 | A1 | 1/2009 | Bundschus et al. |
| 2011/0119212 | A1* | 5/2011 | De Bruin ................. A61B 5/00 706/12 |
| 2012/0116795 | A1* | 5/2012 | Ledley ................... G06Q 50/24 705/2 |
| 2013/0013603 | A1 | 1/2013 | Parker et al. |
| 2013/0091126 | A1 | 4/2013 | Krishnaswami et al. |
| 2013/0096946 | A1 | 4/2013 | Shah et al. |
| 2013/0144887 | A1 | 6/2013 | Chen et al. |
| 2014/0280086 | A1* | 9/2014 | Bouadjenek ........ G06F 16/2228 707/723 |
| 2015/0088888 | A1* | 3/2015 | Brennan ................. G06F 16/38 707/737 |
| 2016/0019299 | A1 | 1/2016 | Boloor et al. |
| 2016/0048564 | A1* | 2/2016 | Bassett, Jr. ............ G16B 50/00 715/230 |
| 2016/0210426 | A1 | 7/2016 | Robinson et al. |
| 2016/0232321 | A1* | 8/2016 | Silverman .............. G16H 10/40 |
| 2017/0255743 | A1 | 9/2017 | Torkamani |
| 2018/0081859 | A1* | 3/2018 | Snider ..................... G06F 40/44 |
| 2018/0137249 | A1* | 5/2018 | Eggebraaten .......... G16H 10/60 |
| 2018/0137433 | A1* | 5/2018 | Devarakonda ......... G16H 10/20 |
| 2018/0211174 | A1 | 7/2018 | Allen et al. |
| 2018/0373844 | A1* | 12/2018 | Ferrandez-Escamez .................... G06F 40/284 |
| 2019/0034593 | A1* | 1/2019 | Bouman ............ G06Q 30/0206 |
| 2019/0042563 | A1* | 2/2019 | Pestian ................. G06F 40/205 |
| 2019/0130073 | A1* | 5/2019 | Sun ........................ G16H 50/70 |
| 2020/0175020 | A1 | 6/2020 | Eifert et al. |
| 2020/0175021 | A1 | 6/2020 | Eifert et al. |
| 2020/0184006 | A1 | 6/2020 | Eifert et al. |
| 2020/0218719 | A1 | 7/2020 | Eifert et al. |
| 2020/0227176 | A1 | 7/2020 | Eifert et al. |

OTHER PUBLICATIONS

List of IBM Patents or Patent Applications Treated as Related dated Mar. 26, 2019.

Tamborero et al., "Cancer Genome Interpreter Annotates the Biological and Clinical Relevance of Tumor Alterations" Genome Medicine (Mar. 28, 2018) 10(25): 8 pages, doi: https://doi.org/10.1101/140475.

Wei et al., "tmVar 2.0: integrating genomic variant information from literature with dbSNP and ClinVar for precision medicine." doi: 10.1093/bioinformatics/btx541. Bioinformatics. Jan. 1, 2018;34(1): pp. 80-87.

Allot et al., "LitVar: A Semantic Search Engine for Linking Genomic Variant Data in PubMed and PMC." Nucleic Acids Research, vol. 46. Web Server issue (2018): W530-W536. PMC. Web., Aug. 15, 2018, 7 pages.

Wei et al., "GNormPlus: An Integrative Approach for Tagging Genes, Gene Families, and Protein Domains." BioMed Res Int 2015, vol. 2015, Article ID 918710, http://dx.doi.org/10.1155/2015/918710, Sep. 2015, 7 pages.

Seva et al., "Track 4: Mining protein interactions and mutations for precision medicine (PM)," BioCreative, 2017. www.biocreative.org/media/store/files/2018/BC6_track4_13.pdf, 5 pages.

Yepes et al., "Mutation extraction tools can be combined for robust recognition of genetic variants in the literature" [version 2; referees: 2 approved, 1 approved with reservations]. F1000Research 2014, 3:18 (doi: 10.12688/f1000research.3-18.v2), Nov. 2017, pp. 1-27.

Ravikumar et al., "Text Mining Facilitates Database Curation—Extraction of Mutation-Disease Associations from Bio-Medical Literature." BMC Bioinformatics, 16 (2015): 185, pp. 1-15.

Asma et al., "DiMeX: A Text Mining System for Mutation-Disease Association Extraction." PLoS ONE, 11(4): e0152725, 2016, 26 pages.

LexisNexis, "Developing a Search with LexistNexis." © 2014 LexisNexis. NBI01326-0 0414, https://www.lexisnexis.com/bis-user-information/docs/developingasearch.pdf, pp. 1-17.

U.S. National Library of Medicine, "Search Strategy Used to Create the Systematic Reviews Subset on PubMed," 2018, https://www.nlm.nih.gov/bsd/pubmed_subsets/sysreviews_strategy.html, Accessed Aug. 17, 2018, 2 pages.

U. S. National Library of Medicine, "PubMed Help," Bookshelf ID: NBK3827, 2018, https://www.ncbi.nlm.nih.gov/books/NBK3827, National Center for Biotechnology Information, Accessed Aug. 17, 2018, 125 pages.

Weng et al., "Medical Subdomain Classification of Clinical Notes Using a Machine Learning-Based Natural Language Processing Approach." BMC Medical Informatics and Decision Making 17 (2017): 155. PMC. Web., Aug. 16, 2018, pp. 1-13.

Kafkas et al., "Section Level Search Functionality in Europe PMC." Journal of Biomedical Semantics 6 (2015): 7. PMC. Web. Aug. 16, 2018, pp. 1-5.

Hofmann et al., "The impact of document structure on keyphrase extraction." In Proceedings of the 18th ACM conference on Information and knowledge management (CIKM '09). ACM, New York, NY, USA, 2009, pp. 1725-1728.

Xu et al., "A semi-supervised approach to extract pharmacogenomics-specific drug-gene pairs from biomedical literature for personalized medicine," Journal of Biomedical Informatics, vol. 46, Issue 4, 2013, pp. 585-593.

Lee et al., "Deep learning of mutation-gene-drug relations from the literature." BMC Bioinformatics (2018), 19:21. Published: Jan. 25, 2018, pp. 1-13.

Huang et al., "Predicting drug efficacy based on the integrated breast cancer pathway model," 2011 IEEE International Workshop on Genomic Signal Processing and Statistics (GENSIPS), San Antonio, TX, Dec. 2011, pp. 42-45.

Artemov et al., "A Method for Predicting Target Drug Efficiency in Cancer Based on the Analysis of Signaling Pathway Activation." Oncotarget, vol. 6, No. 30, www.impactjournals.com/oncotarget/, Aug. 2015, pp. 29347-29356.

Allafiyari et al., "A Brief Survey of Text Mining: Classification, Clustering and Extraction Techniques", https://arxiv.org/pdf/1707.02919.pdf, Cornell Library University, arXiv:1707.02919v2 [cs.CL], Jul. 28, 2017, 13 pages.

(56) References Cited

OTHER PUBLICATIONS

Clematide et al., "Ranking Relations between Diseases, Drugs and Genes for a Curation Task", Journal of Biomedical Semantics, https://jbiomedsem.biomedcentral.com/articles/10.1186/2041-1480-3-S3-S5, Oct. 5, 2012, pp. 1-22.
Wu et al.; "Ranking Gene-Drug Relationships in Biomedical Literature using Latent Dirichlet Allocation", NCBI, https://www.ncbi.nlm.nih.gov/pmc/articles/PMC4095990/: Pac Symp Biocomput, Author manuscript, Jul. 14, 2014, pp. 1-15.
Chen et al., "IBM Watson: How Cognitive Computing Can Be Applied to Big Data Challenges in Life Sciences Research". Clinical Therapeutics, 2016, 38(4):688-701. doi: 10.1016/j.clinthera.2015.12.001. Epub Apr. 21, 2016, pp. 688-701.
NCBI, "PubMed", US National Library of Medicine National Institute of Health, 2018; https://www.ncbi.nlm.nih.gov/pubmed/ (accessed Nov. 30, 2018), 2 pages.
U.S. National Library of Medicine, "MEDLINE/PubMed Resources Guide", 2018, https://www.nlm.nih.gov/bsd/pmresources.html (accessed Nov. 30, 2018), 7 pages.

\* cited by examiner

PROCESSING DOCUMENTS IN CONTENT REPOSITORIES TO GENERATE PERSONALIZED TREATMENT GUIDELINES

BACKGROUND

1. Technical Field

Present invention embodiments relate to personalized medicine, and more specifically, to processing documents in content repositories to generate personalized treatment guidelines.

2. Discussion of the Related Art

Content repositories often contain a large corpus of documents of varying types of information. For example, a user may search NCBI's PubMed® database for different types of peer-reviewed scientific and clinical documents. However, content repositories may not classify all types of documents adequately. Additionally, access to full-length research documents in repositories such as PubMed® is often granted only if an institutional license agreement has been implemented with the journal's publisher or another form of payment has been submitted to acquire the rights to the full-length document. To ensure the accuracy of the data, users must be able to evaluate figures, graphs, tables and text within the results section of the documents. In some cases, content repositories may maintain over two million documents with no intelligent way to access the content. Other content repositories do not provide user interfaces for specific content searching. Accordingly, large quantities of information may reside in various content repositories with limited accessibility.

SUMMARY

According to one embodiment of the present invention, a computer system processes documents in a content repository. Each document of a plurality of documents is classified into one of a functional category and a clinical category. Each document is annotated using one or more corpora to generate document annotations. Documents satisfying one or more query terms are identified by comparing each query term to the document annotations. The identified documents are ranked based on a determined relevance. Guidelines are produced based on the ranking of the identified documents. Embodiments of the present invention further include a method and program product for processing documents in a content repository in substantially the same manner described above.

BRIEF DESCRIPTION OF THE DRAWINGS

Generally, like reference numerals in the various figures are utilized to designate like components.

DETAILED DESCRIPTION

Figure 1:
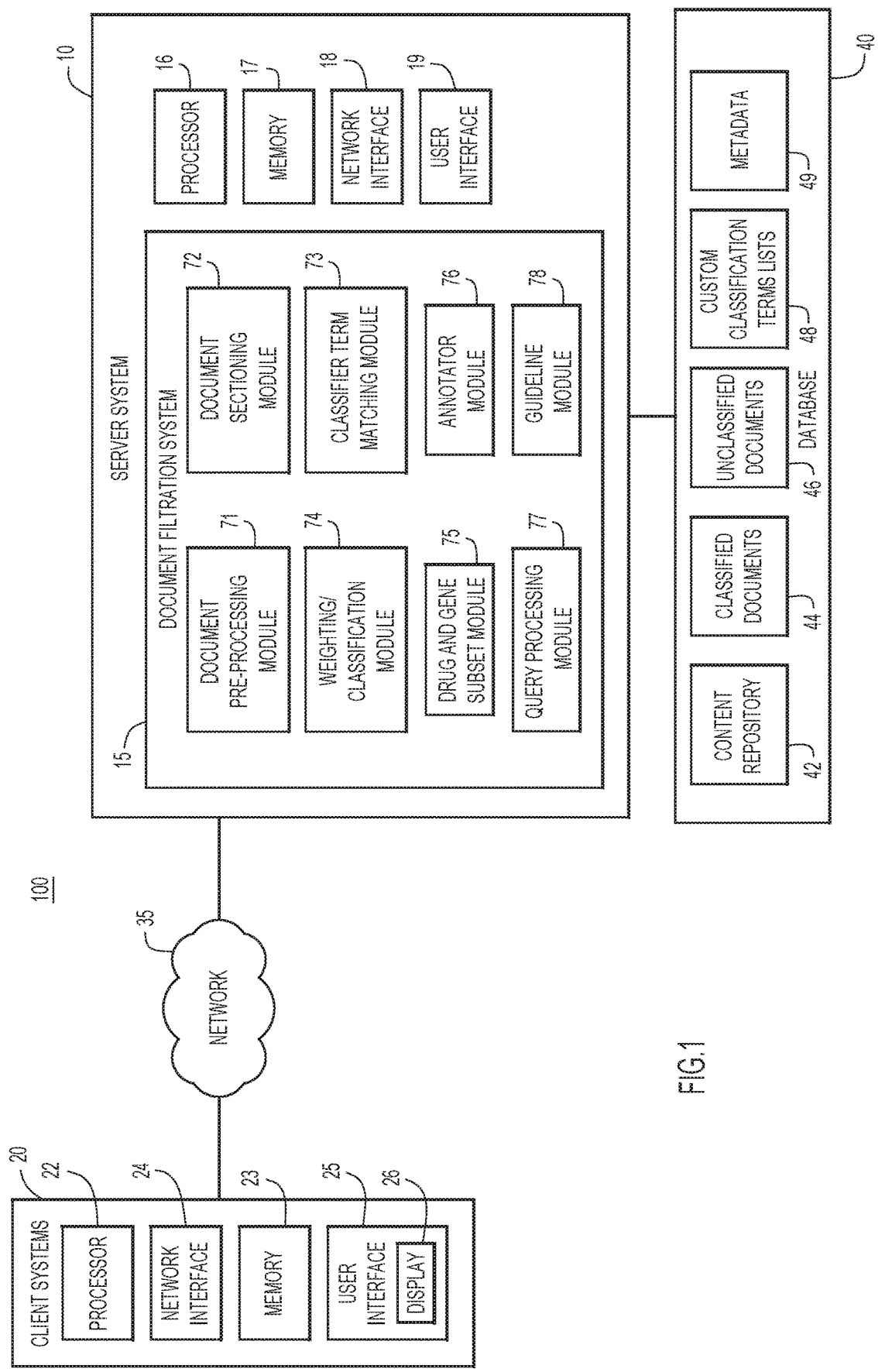
FIG. 1 is a block diagram of an example computing environment for the document filtration system, according to embodiments of the present disclosure.

Present invention embodiments relate generally to personalized medicine, and more specifically, to processing documents in content repositories to generate personalized treatment guidelines. Genomic-based treatment guidelines document disease-specific, pathogenic genomic variants, that can be targeted by one or more drugs to provide superior survival benefits over conventional therapies. For example, personalized treatment guidelines may be developed for a patient who has a particular combination of one or more genes, gene variants, disease types, and resistance mutations, and may also consider any drugs being administered to the patient. Gene variants may include alternative forms of genes, including pathological forms, and resistance mutations may include mutations that can result in acquired resistance to drugs, such as cancer therapies.

Present invention embodiments generate personalized treatment guidelines by processing large volumes of documents found in content repositories, such as NCBI's PubMed® database. In particular, documents are classified into evidence categories (such as functional or clinical), and documents are then annotated based on the presence of particular words or phrases of interest in various sections of the documents. A machine learning model that integrates patient details, such as genes, gene variants, disease types, resistant mutations, and/or drugs, may predict which annotated documents contain information that is relevant to patients with all types of diseases. A priority scoring procedure that is either rules-based, or constructed using a machine learning model, is incorporated to predict which evidence from individual documents can be extracted to produce a disease ontology based on genomic evidence to guide clinical decision-making and management in precision medicine. Thus, present invention embodiments generate treatment guidelines that are personalized to an individual.

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of embodiments of the invention as set forth hereinafter.

An example environment for use with present invention embodiments is illustrated in FIG. 1. Specifically, the environment includes one or more server systems 10, and one or more client or end-user systems 20. Server systems 10 and client systems 20 may be remote from each other and communicate over a network 35. The network may be implemented by any number of any suitable communications media (e.g., wide area network (WAN), local area network (LAN), Internet, Intranet, etc.). Alternatively, server systems 10 and client systems 20 may be local to each other, and communicate via any appropriate local communication medium (e.g., local area network (LAN), hardware, wireless link, Intranet, etc.).

Client systems 20 enable users to access documents (e.g., functional documents, clinical documents, case studies, review articles, or meeting and proceeding abstracts, etc.) from server systems 10 for analysis and review. The server system may include a document filtration system 15 to classify documents in order to select and prioritize relevant information. A user of a client system 20 may provide queries to server 10. A user may input one or more query terms, which are processed by server 10 and its various modules. Upon processing a query, server 10 may return results to client device 10, including personalized treatment guidelines corresponding to the query. Client device 10 may also enable a user to access content repository 42 in order to access documents stored in database system 40.

A database system 40 may store various information for the filtration (e.g., content repository 42, classified documents 44, unclassified documents 46, custom classification terms lists 48, metadata 49, etc.). The database system may be implemented by any conventional or other database or storage unit, may be local to or remote from server systems 10 and client systems 20, and may communicate via any appropriate communication medium (e.g., local area network (LAN), wide area network (WAN), Internet, hardwire, wireless link, Intranet, etc.). The client systems may present a graphical user (e.g., GUI, etc.) or other interface (e.g., command line prompts, menu screens, etc.) to solicit information from users pertaining to the desired documents and filtration, and may provide reports including filtration results (e.g., percentage of documents classified into a respective category, percentage of documents not classified into a respective category, number of terms of a custom classification terms list found in a document, etc.).

Server systems 10 and client systems 20 may be implemented by any conventional or other computer systems preferably equipped with a display or monitor 26, a base (e.g., including at least one processor 16, 22 one or more memories 17, 23 and/or internal or external network interfaces or communications devices 18, 24 (e.g., modem, network cards, etc.)), optional input devices (e.g., a keyboard, mouse or other input device) and/or user interface 19, 25 and any commercially available and custom software (e.g., server/communications software, document filtration system 15, browser/interface software, etc.).

Alternatively, one or more client systems 20 may analyze documents to determine document classification when operating as a stand-alone unit. In a stand-alone mode of operation, the client system stores or has access to the content repository 42 and custom classification terms lists 48 as well as the document filtration system 15. The graphical user (e.g., GUI, etc.) or other user interface (e.g., command line prompts, menu screens, etc.) may solicit information from a corresponding user pertaining to the document filtration, and may provide reports including classification results and document ranking (e.g., percentage of documents classified into a respective category, percentage of documents not classified into a respective category, number of terms of a custom classification terms list found in a document, etc.).

Document filtration system 15 may include one or more modules or units to perform the various functions of present invention embodiments described below. The various modules (e.g., document pre-processing module 71, document sectioning module 72, classifier term matching module 73, weighting/classification module 74, drug and gene subset module 75, annotator module 76, query processing module 77, guideline module 78, etc.) may be implemented by any combination of any quantity of software and/or hardware modules or units, and may reside within memory 17 of the server and/or client systems for execution by processor 16.

The document pre-processing module 71 may render the documents readable by a machine reader. In some aspects, optical character recognition may be used to recognize text in a document, to render the text readable and searchable. Additionally, text in tables, images, image captions, or lists may also be rendered machine readable. This processing ensures that images of documents, e.g., scanned PDFs, are included in the analysis.

The drug and gene subset module 75 filters content (documents) of the content repository 42 to generate drug subsets and gene subsets of documents. A list of drugs or genes may be obtained, for example, by a subject matter expert, and used to filter the content of the content repository. If a drug name is found in a document, that document is added to the document subset of drugs. If a gene name is found in a document, that document is added to the document subset of genes. In some aspects, the documents may be preprocessed using the preprocessing module 71 prior to filtration by module 75. The document subsets may be provided to the document sectioning module for further processing and analysis. Similar operations may be performed for other entities including gene name synonyms, gene variant name synonyms, drug name synonyms, and cancer-type name synonyms.

The document sectioning module 72 may be used to identify sections of machine readable documents. In some aspects, a document section may identified by an appropriate header. For example, the header "abstract" may indicate the presence of an abstract. The header "introduction" or "background" may indicate the presence of a section describing the current state of the art and/or background to help the reader better understand the context and rationale of the current study. The header "material and methods" may indicate an experimental section that describes the materials and methods and experimental protocols used during the course of experiments. The header "results" may indicate the presence of a results section showing data generated from the experiments. The header "discussion" may indicate the presence of a discussion section which interprets the experimental results. The header "conclusion" may indicate a summary of the experimental results of the document and future areas of investigation.

In some aspects, a section labeled with a header may be further divided into subsections having sub-headings. For example, the abstract may additional contain sub-headers such as "objective", "methods", "results", and "conclusion". In some aspects, subsections of specific subheadings may be targeted to analyze content for specific custom classification terms.

The classifier term matching module 73 may search specific sections of each document for terms in a custom classification terms list. For example, a clinical classification term list may contain single terms or phrases that may be used to identify the document as a clinical document. As another example, a functional classification term list may contain single terms or phrases that may be used to identify the document as a functional document. Similar term lists may be provided for review articles, conference proceedings and abstracts, and case studies. In some aspects, both functional and clinical information may be needed to determine the significance of a given biologic relationship. Functional information provides evidence regarding a gene's and/or gene variant's function, while clinical information provides evidence regarding a patient's response to treatment with a targeted therapy (clinical studies). For instance, the materials and methods section may be searched with custom-designed "functional query terms" to identify and classify functional articles. The abstract may be searched with custom-designed "clinical query terms" to identify and classify clinical articles.

The weighting/classification module 74 may classify different documents within the content repository and documents within document subsets into different categories. In some aspects, weighting scores may be used to classify documents as functional or clinical documents. Based on the number of terms or phrases identified in the specific section(s) of the document, a weighting score may be determined (see, FIG. 3). If the weighting score is above a classification threshold value, then the document may be classified into a respective category. Documents may be ranked for presentation to the user based upon the number of times a unique classification term appears in the methods section (for functional articles) or in the abstract section (for clinical articles). The weighting classification module 74 may also classify documents into respective categories (e.g., case study, review article, or conference proceedings and abstract) based on article type tags and/or weighting scores.

In some aspects, once classified, the documents may be stored in designated locations within database 40 (e.g., within classified documents 44), such that functional documents are located in a first directory, clinical documents are located in a second directory, and so forth. Alternatively, documents may be maintained in the same location within the content repository, but associated with metadata 49 that indicates whether the document is classified and the respective category that the document has been classified into.

Documents that the system is not able to classify may be stored in unclassified documents 46. In some aspects, these documents may be moved into a corresponding directory for unclassified documents. Alternatively, documents may be maintained in the same location within the content repository, but associated with metadata 49 that indicates that the documents are unclassified. These documents may be subject to manual review.

Annotator module 76 may classify documents that are located in a content repository into one or more categories, and may annotate sections of documents based on their classification. Annotator module 76 accesses one or more content repositories, such as content repository 42, in order to retrieve information relating to documents, such as text of sections of the documents, metadata associated with documents, and the like. Documents may be classified into either a functional category or a clinical category. Both functional and clinical information may be needed to determine the significance of a given biologic relationship. Functional information provides evidence relating to a gene's and/or gene variant's function, and clinical information provides evidence regarding a patient's response to treatment with a targeted therapy (e.g., in clinical studies). For instance, a materials and methods section may be searched with a corpus of functional query terms to identify and classify functional articles. An abstract section of a document may be searched with a corpus of clinical query terms to identify and classify clinical articles.

In some embodiments, annotator module 76 provides weighting scores to classify each documents into a functional category or a clinical category. Based on the number of terms or phrases identified in the specific section(s) of the document, a weighting score may be determined. If the weighting score is above a classification threshold value, then the document may be classified into a respective category. Annotator module 76 may also classify documents into respective categories (e.g., functional, clinical, case reports, review articles, or meetings and proceedings abstracts) based on article type tags and/or weighting scores.

Annotator module 76 may annotate documents using a corpus of words and/or phrases that is selected based on each document's category. In some embodiments, annotator module 76 utilizes conventional or other natural language processing techniques to annotate documents. Documents may be classified as either functional or clinical according to the presence of functional or clinical terms in each document.

Once documents are classified as functional or clinical, the documents may be scored and subsequently ranked based on the focus of each document. All specified sections of a document may be searched using custom dictionaries that include gene terms, targeted drug terms, disease type terms, and gene variant terms. Each document may be assigned a score based on the frequency that terms appear in a document. Once the documents are scored, the documents may be ranked according to the gene score, targeted drug score, disease type score, and gene variant score of each document. In some embodiments, the scores may receive different weights. Thus, annotator module 76 may rank functional and clinical documents by gene names, targeted drug names, disease types, and gene variant names.

Annotator module 76 may utilize natural language processing to identify disease biomarkers that are referenced in functional and clinical documents, and rank documents accordingly. In some embodiments, annotator module 76 use a natural language processing rules-based model to autonomously annotate abstracts of pre-classified functional or clinical documents to identify biomarkers relating to diagnosis, prognosis, predisposition, drug resistance, and predicted response to therapies of diseases such as cancers. Any additional information that may be relevant to clinical decision-making, such as gene signaling and pathway activation, immunotherapies, and the like, may also be identified. Each annotation may be associated with a score that represents the weight of the annotation's value in a clinical decision-making process.

Annotator module 76 may employ machine learning techniques to predict the most significant biomarkers for a disease type. In some embodiments, annotator module 76 utilizes a neural network to determine which biomarkers are correlated to particular disease types. In order to identify associations between biomarkers and disease types, annotator module 76 may use a corpus of any functional and clinical documents that have a biomarker score above a predefined threshold.

Annotator module 76 may use a machine learning model to predict which of the drugs that target the same biomarker may be the most effective for a particular disease type. In some embodiments, annotator module 76 utilizes a neural network to determine the efficacy of drugs for targeting a selected disease type. In order to identify drugs that will be effective against a disease type, annotator module 76 may use a corpus of any functional and clinical documents that have a biomarker score above a predefined threshold.

Annotator module 76 may annotate documents using a corpus that includes one or more of genes, gene variants (e.g., mutations such as single-nucleotide polymorphisms), fusion genes (e.g., hybrid genes formed from two or more previously separate genes), disease types, resistance mutations, drugs, biomarkers, and the like. In some embodiments, annotator module 76 annotates the sections of documents once the documents are classified. Annotator module 76 may utilize separate corpora for various sections of documents.

Query processing module 77 receives and processes queries against the annotation information. A query may contain one or more terms, such as one or more gene terms, gene variant terms, disease terms, resistant mutation terms, and/or drug terms. In general, query processing module 77 calculates a priority score for each document for a given query, and ranks the documents using the priority score in order to select documents that are relevant to the query terms. The priority score of a document may correspond to the frequency in which a query term appears in the document, which query processing module 77 may ascertain by consulting the annotation information generated by annotator module 76. In calculating a priority score for a document, a term may be weighted according to the section of a document in which the term appears. For example, a query term appearing in the title of a document may be weighted more heavily than the same term appearing in the abstract. Query processing module 77 may be provided with a list of synonymous terms, so that different synonyms of the same query term may be counted when calculating a priority score. For example, if a query contains a brand name of a drug, any documents that discuss the drug using the generic name will be prioritized as equally as documents using only the brand name or both names.

Documents may be ranked according to priority scores by prioritizing articles that mention queried gene names the greatest number of times, with differential weightings applied based on whether the gene name appears in the title section, the abstract section, or the results section. Additionally or alternatively, documents may be ranked according to priority scores by prioritizing documents that mention queried disease types the most times, with differential weightings applied based on whether the disease name appears in the title section, the abstract section, or the introduction section. Documents may also be ranked according to priority scores by prioritizing articles that mention queried drug names the most number of times, with differential weightings applied based on whether the drug names appear in the title section, the abstract section, or the introduction section. In some embodiments, query processing module 77 ranks documents using a combined approach in which documents are prioritized that mention all (or most) of the query terms, with differential weightings applied based on the sections of the documents in which the query terms appear.

Query processing module 77 may rank documents using conventional or other machine learning techniques to identify documents that discuss relationships between query terms. In some embodiments, query processing module 77 uses a neural network to prioritize documents that may be used as evidence to support relationships between two or more query terms.

After documents are ranked based on the number and types of annotations extracted from each document, text that is associated with any of five biomarker types (diagnostic biomarkers, prognostic biomarkers, predisposing biomarkers, drug resistance biomarkers, and biomarkers relating to predicted responses to therapies) is extracted from the documents that have been pre-classified as clinical documents or functional documents. Clinically-relevant information may be placed into predetermined and relevant categories, including clinical data, pre-clinical data, gene activity and signaling pathway data, a disease status category, and the like. The categorized information may then be used to produce genomic-based guidelines to support clinical decision-making.

Guideline module 78 may assemble ranked documents into a levels of evidence hierarchy in order to produce personalized treatment guidelines based on terms of a query. There may be separate levels of evidence that correspond to the number of query term categories that a document matches. One level of evidence may contain documents that match at least one gene term in the query, another level of evidence may contain documents that match at least one gene term and gene variant term, another level of evidence may contain documents that match at least one gene term, gene variant term, and disease type term, another level of evidence may contain documents that match at least one gene term, a gene variant term, disease type term, and drug term, and another level of evidence may contain documents that match at least one gene term, a gene variant term, disease type term, drug term, and resistance mutation term.

Guideline module 78 may generate a levels of evidence hierarchy that contains levels corresponding to one or more query term categories, and documents that support the query at that level. The documents may be presented in an order corresponding to the ranking of the documents as determined by query processing module 77. Guideline module 78 may include documents in the levels of evidence hierarchy that surpass a predetermined priority score. Additionally or alternatively, guideline module 78 may populate a levels of evidence hierarchy with the a predetermined number of documents ranked according to priority score; for example, each level of evidence may contain the top three documents that support that level of evidence. In some embodiments, guideline module 78 may list documents according to an identifier, such as the title of the document, the title of the document and one or more author names, and/or any other form of citation. Additionally or alternatively, guideline module 78 may fetch all or a portion of the text of documents that are included in a levels of evidence hierarchy. For example, guideline module 78 may provide the abstract of each document, the introduction of each document, and the like.

FIGS. 2A-2E show various flow charts for classifying documents or document subsets into respective categories. Different types of documents (e.g., scientific publications and clinical articles, review articles, case reports, or meeting/proceeding abstracts, etc.) have certain physical publishing layout requirements including providing various types of data in discrete sections of the document, typically in a predefined order. Sections of the document may also be defined by the publishing requirements, and may include the title, abstract, introduction, materials and methods, analysis/results, and discussion/conclusion sections. These documents may reside in a content repository, wherein the documents are not classified into a category.

According to present invention embodiments, the documents are rendered machine readable, so that the headings and corresponding text can be processed by the filtration system 15. Each section may contain specific types of information. Accordingly, limiting the search for custom classification terms to particular sections ensures that the documents are classified correctly.

A rules-based model may be used to search in specific sections of a document to classify the type of document (e.g., an unstructured biomedical research article). The sectioned documents can be searched, for example, for user defined custom classification terms within the text of specific sections. Based on the search results, the filtration system can classify the documents in the content repository into a respective category. The rules-based filtering system is configured to search in specific sections of a document to ensure the data originated in the current study, rather than being provided as a reference to another document.

Figure 2A:
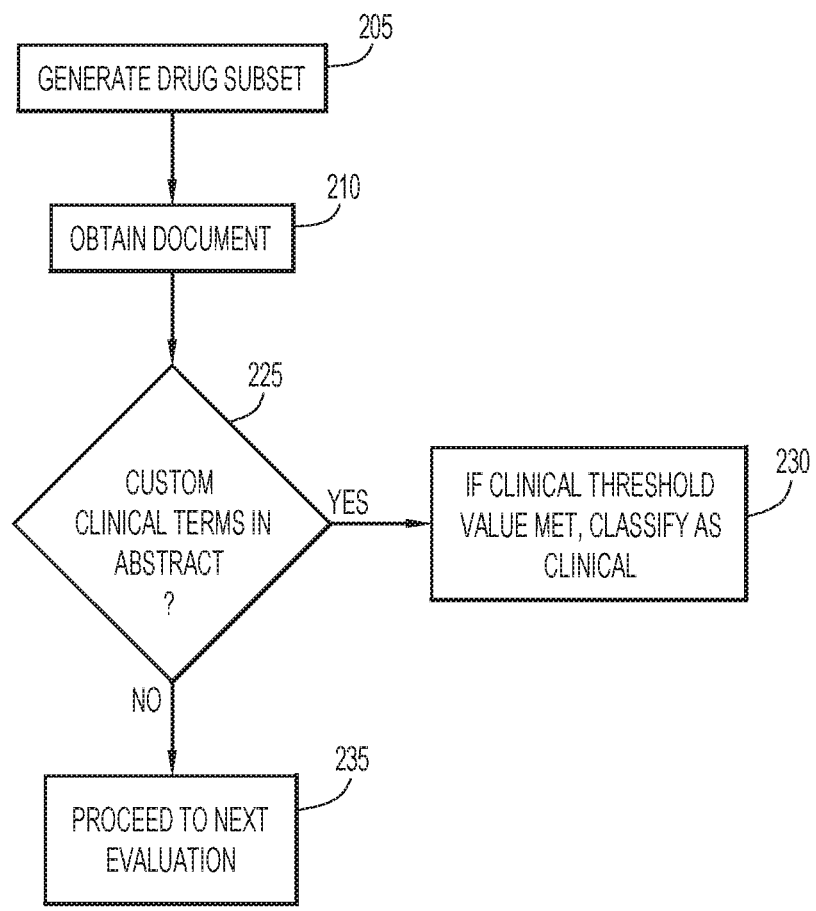
FIGS. 2A-2E are flow diagrams showing classification of a document into a respective category of documents, according to embodiments of the present disclosure.

FIG. 2A shows a flowchart for classifying clinical documents or document subsets. Clinical documents may provide evidence that a specific biologic relationship has important therapeutic ramifications. For example, a clinical document may contain a phrase such as "overexpression of erbb2 causes breast cancer" or "pertuzumab increases the rate of pathological complete response HER2-positive breast cancer".

To identify clinical documents, a drug subset of documents is generated at operation 205. A list of drug names may be provided to the drug and gene subset module 75, from the custom classification terms lists 48. Documents of the content repository are filtered using the list of drug names, and if a term (drug name) is found, the document is added to the drug subset of documents. At operation 210, a document is obtained from the content repository. At operation 225, a particular section of the document (e.g., the abstract section) may be searched for custom clinical classification terms and/or phrases. For example, a clinical filter comprising custom classification terms or phrases may be applied to the abstract portions of the documents of the content repository to identify clinical documents. If a threshold condition is met (e.g., the weighting score is greater than a clinical threshold value), at operation 230, the document is classified as clinical. Otherwise, the document may be evaluated for classification into a different category (e.g., functional, case study, review article, conference type and proceedings abstract, etc.) at operation 235.

In some aspects, the document may be moved into a directory associated with clinical documents. Alternatively, the document may remain in the content repository and may be associated with metadata indicating that the document is a clinical document.

Figure 2B:
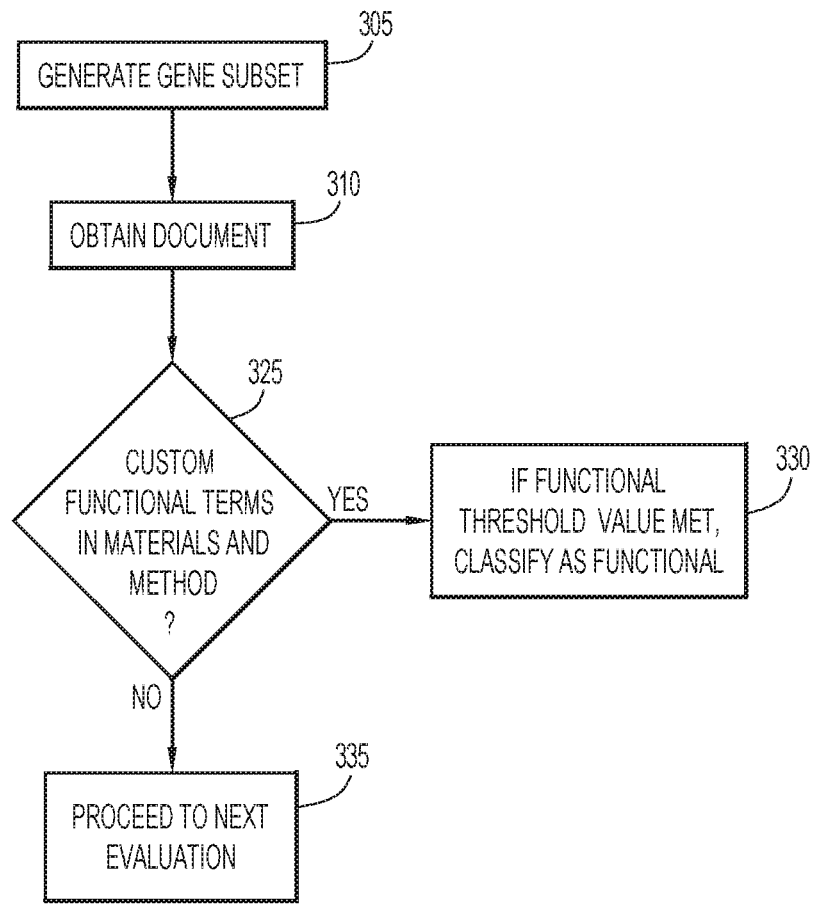

FIG. 2B shows a flowchart for classifying functional documents. Functional documents may provide evidence that a specific genomic alteration is oncogenic or promotes oncogenic properties. For example, a functional document may contain a phrase such as "HER2 transmembrane domain mutations (V659/G660) that stabilize homo- and heterodimerization are rare oncogenic drivers". To identify functional documents, the materials and methods section may be searched using a functional filter for custom functional classification terms.

To identify functional documents, a gene subset of documents is generated at operation 305. A list of gene names may be provided to the drug and gene subset module 75, from the custom classification terms lists 48. Documents of the content repository are filtered using the list of gene names, and if a term (gene name) is found, the document is added to the gene subset of documents. At operation 310, a document is obtained from the content repository. At operation 325, a particular section of the document (e.g., the methods and materials section) may be searched for custom functional classification terms and/or phrases. For example, a functional filter comprising custom classification terms or phrases may be applied to the materials and methods portions of the documents of the content repository to identify functional documents. If a threshold condition is met (e.g., the weighting score is greater than a functional threshold value), at operation 330, the document is classified as functional. Otherwise, the document may be evaluated for classification into a different category (e.g., clinical, case study, review article, conference type and proceedings abstract, etc.) at operation 335. In some aspects, the document may be moved into a directory associated with functional documents. Alternatively, the document may remain in the content repository and may be associated with metadata indicating that the document is a functional document.

Figure 2C:
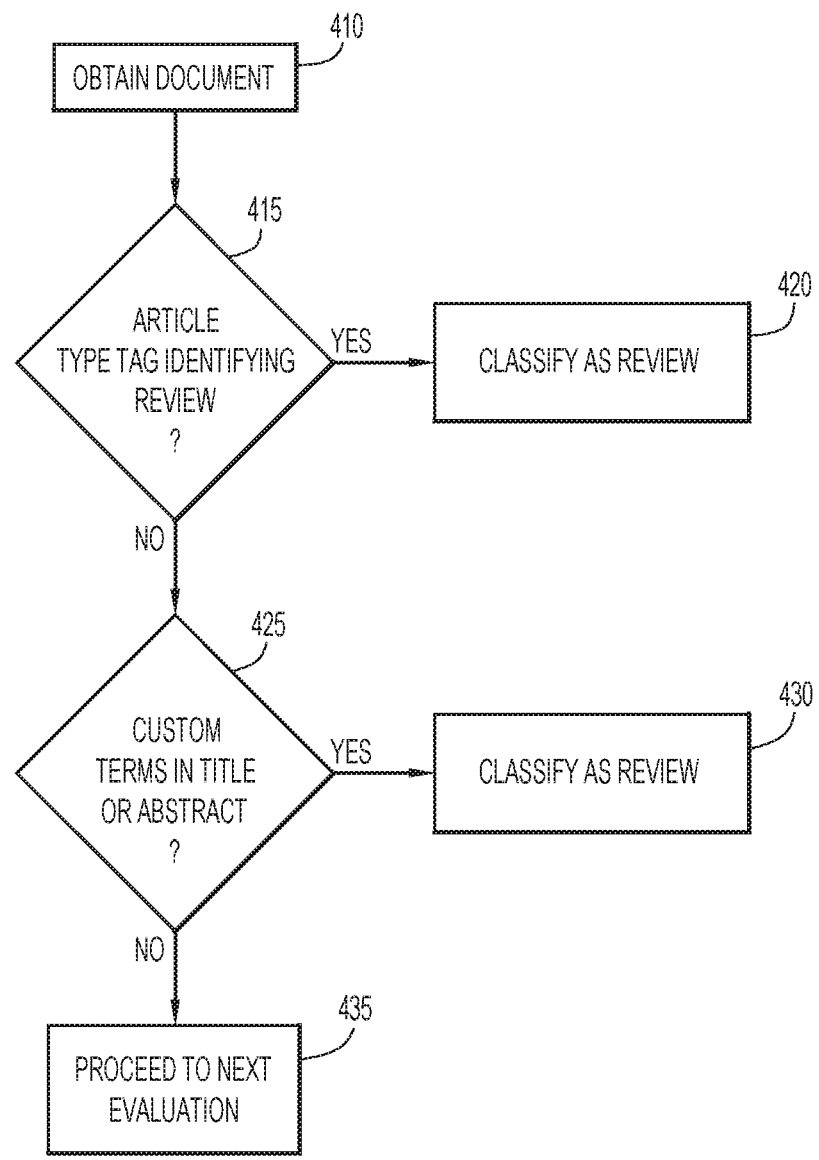

FIG. 2C shows a flowchart for classifying review articles. Review articles may summarize other research documents. For example, a review article may contain references to a plurality of other research documents with a related theme, such as "Kidney Cancer: Recent Advances and Future Directions". To identify review articles, the cover page, title, or header may be searched using a review filter for custom review classification terms.

To identify review articles, a document is obtained from the content repository at operation 410. At operation 415, the system determines whether an article type tag is associated with the document that indicates that the document is a review article. In some cases, review articles, conference proceedings and abstracts, and case studies may have an article type tag identifying the type of article. In other cases, clinical and functional studies may not have an article type tag as these categories of documents may contain both types of information in different sections. If such a tag is found, at operation 420, the system classifies the document as a review article. If an article type tag is not found, a particular section of the document (e.g., the title, cover page, headings) may be searched for custom review classification terms and/or phrases at operation 425. For example, a review filter comprising custom classification terms or phrases may be applied to the cover page, title, or headers of the documents of the content repository to identify review articles. For example, review articles generally include the phrase "review article" or equivalent on their front/cover page to indicate that the document is a review article. If a review article term is present, at operation 430, the document is classified as a review article. Otherwise, the document may be evaluated for classification into a different category (e.g., functional, case study, clinical, conference type and proceedings abstract, etc.) at operation 435.

In some aspects, the document may be moved into a directory associated with review articles. Alternatively, the document may remain in the content repository and be associated with metadata indicating that the document is a review article.

Figure 2D:
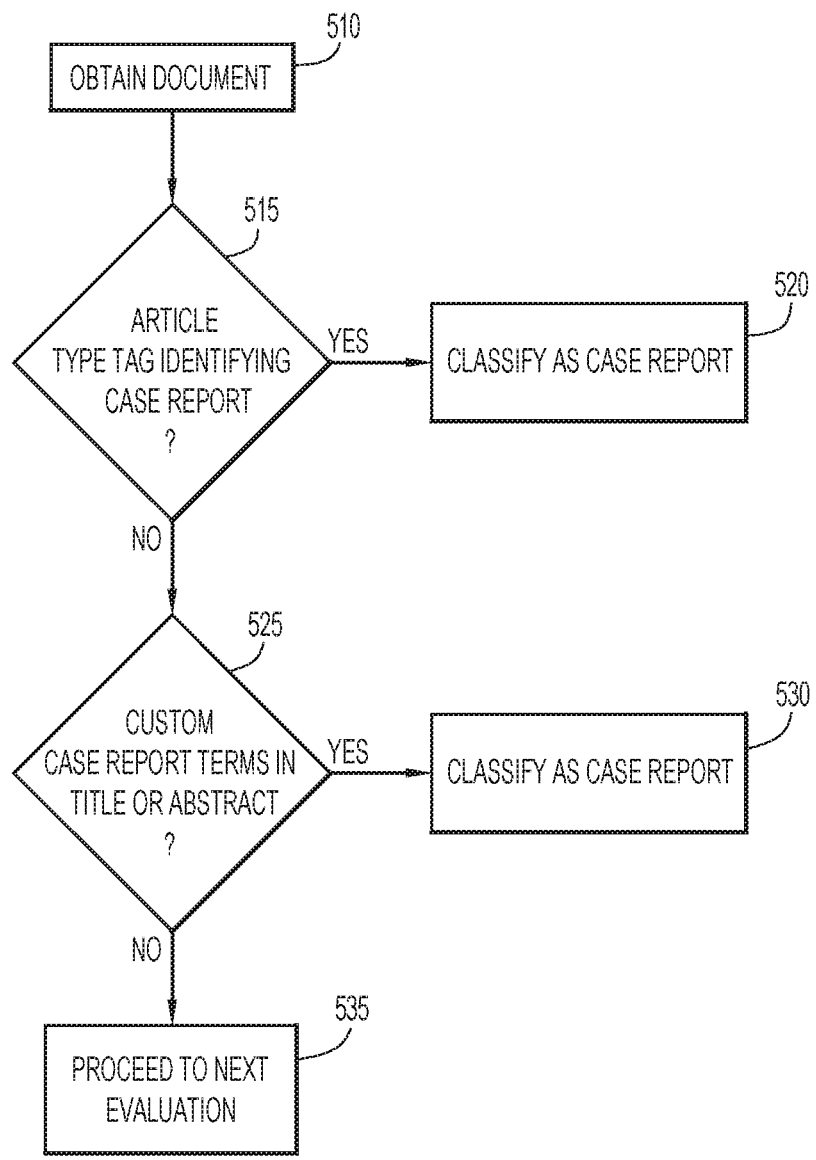

FIG. 2D shows a flowchart for classifying case reports. Case reports may provide information about a single patient, or in some cases, a small number of patients. These documents may not contain a large enough sample size representative of a population, and therefore, may skew data if not properly identified. For example, a case report (or case summary) may discuss a single patient outcome, such as "Kartagener syndrome—case report". To identify case reports, the cover page, title, or header may be searched using a case report filter for custom case report classification terms.

To identify a case report, a document is obtained from the content repository at operation 510. At operation 515, the system determines whether an article type tag is associated with the document that indicates that the document is a case report. An article type tag is typically a numeric identifier associated with documents in a database such as PubMed® or Medline® that identifies the document as a case report. If such a tag is found, at operation 520, the system classifies the document as a case report. If an article type tag is not found, a particular section of the document (e.g., the title, cover page, headings) may be searched for custom review classification terms and/or phrases at operation 525. For example, a case report filter comprising custom classification terms or phrases may be applied to the cover page, title, or headers of the documents of the content repository to identify a case report. For example, a case report generally include the phrase "case report" on their front/cover page to indicate that the document is a case report. If a case report term is present, at operation 530, the document is classified as a case report. Otherwise, the document may be evaluated for classification into a different category (e.g., functional, review article, clinical, conference type and proceedings abstract, etc.) at operation 535.

In some aspects, the document may be moved into a directory associated with case reports. Alternatively, the case report may remain in the content repository and be associated with metadata indicating that the document is a case report.

Figure 2E:
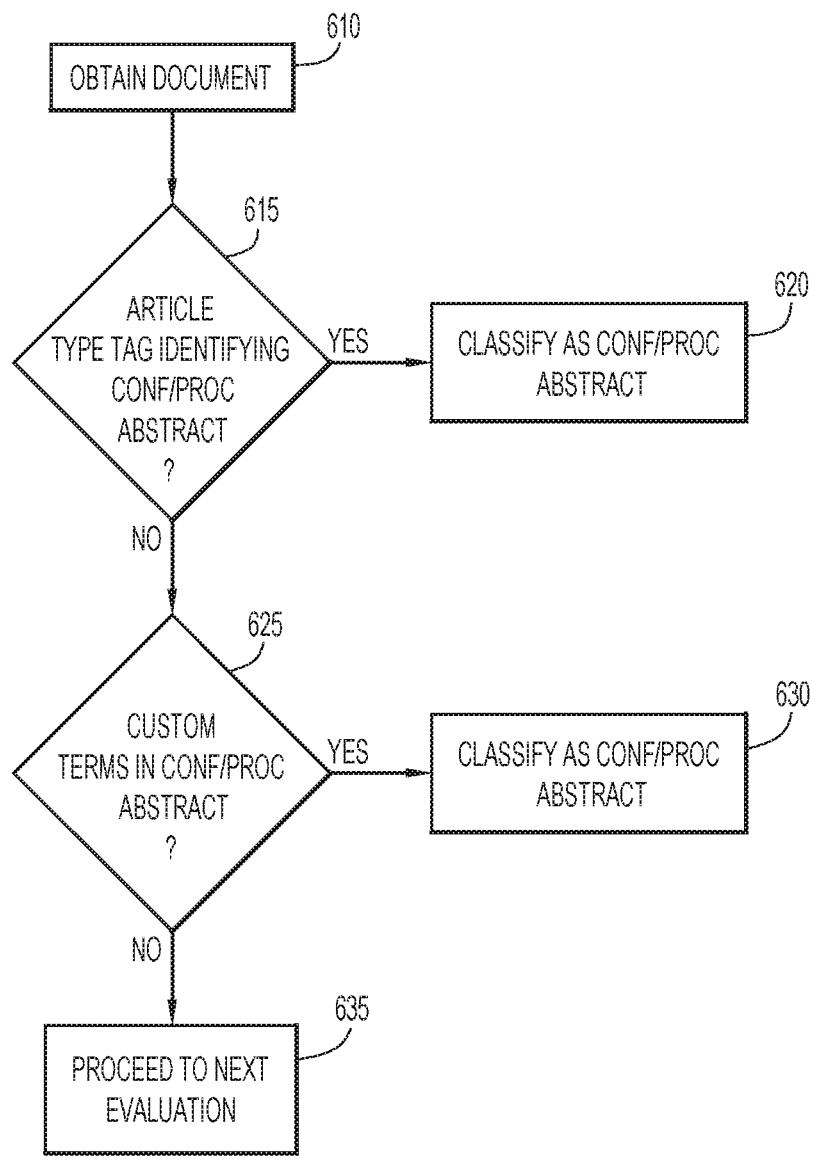

FIG. 2E shows a flowchart for classifying conference proceedings and abstracts. Conference proceedings and abstracts are short documents providing an overview of a presentation or poster from a conference. For example, conference proceedings and abstracts may contain a short summary of a research topic, such as "12th Annual Biotechnology Meeting: abstract collection". To identify conference proceedings and abstract documents, the cover page, title, or header may be searched using a conference proceedings and abstract filter for custom conference proceedings and abstract classification terms.

To identify conference proceedings and abstract documents, a document is obtained from the content repository at operation 610. At operation 615, the system determines whether an article type tag is associated with the document that indicates that the document is a conference proceedings and abstract article. If such a tag is found, at operation 620, the system classifies the document as a conference proceedings and abstract document. If an article type tag is not found, a particular section of the document (e.g., the title, cover page, headings) may be searched for custom conference proceedings and abstract classification terms and/or phrases at operation 625. For example, a conference proceedings and abstract filter comprising custom classification terms or phrases may be applied to the cover page, title, or headers of the documents of the content repository to identify conference proceedings and abstract documents. For example, conference proceedings and abstract documents generally include the phrase "conference proceeding" or abbreviation corresponding to the same on their front/cover page to indicate that the document is a conference proceedings and abstract. If a conference proceedings and abstract term is present, at operation 630, the document is classified as a conference proceedings and abstract. Otherwise, the document may be evaluated for classification into a different category (e.g., functional, review article, clinical, case report, etc.) at operation 635.

In some aspects, the document may be moved into a directory associated with conference proceedings and abstract documents. Alternatively, the document may remain in the content repository and be associated with metadata indicating that the document is a conference proceedings and abstract article.

In some aspects, a document may be classified both as a clinical document and as a functional document. In general, review articles, case reports and meeting/proceeding abstracts will not overlap in regards to classification. Classification may be performed in any evaluation order, such that the document may be evaluated with regard to the order shown in FIGS. 2A-2E, or any other suitable order, and have any quantity of classifications.

Once all evaluations have been performed, then the process may terminate. Documents that are not identified, remain unclassified.

Figure 3:
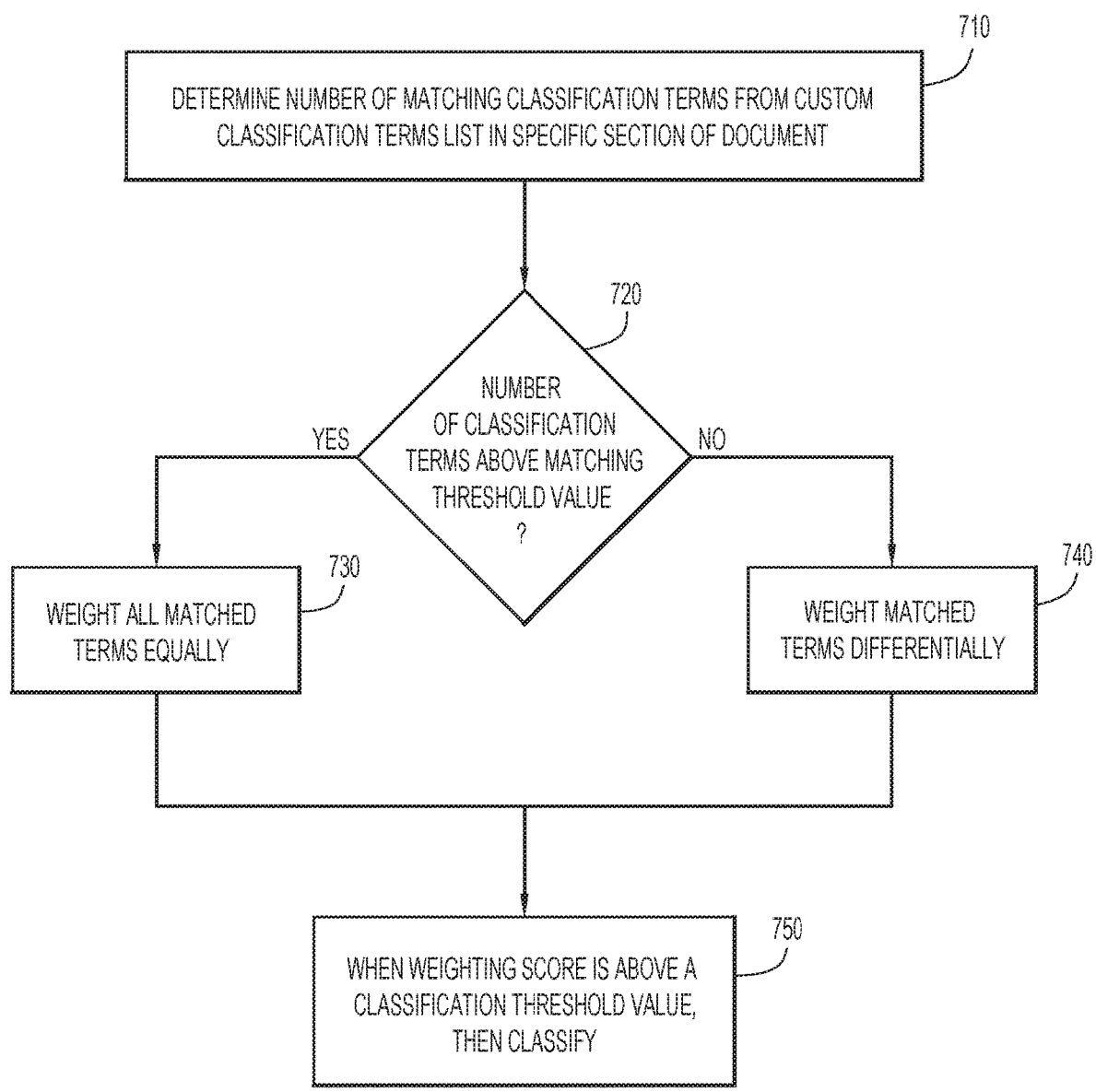
FIG. 3 is a flow diagram showing weighting of matching classification terms from a custom classification terms list for classification of the document, according to embodiments of the present disclosure.

FIG. 3 shows example operations of weighting matched classification terms (e.g., terms from a custom classification terms list that are found in a section of a document) for classification of the document. Custom classification terms may be weighted equally or differentially, as shown in FIG. 3, and results may be aggregated to determine classification of the document.

At operation 710, the number of matching classification terms of a custom classification terms list for a specific section of the document is determined. If the number of unique terms is above a matching threshold value (e.g., seven or more unique terms), all terms are weighted equally, at operation 730. If the weighting score (e.g., a sum of each unique term times a weighting factor of 1) is above a classification threshold value, then the document is classified accordingly at operation 750. If the custom classification terms list is a functional terms list, then the document is classified as a functional document. If the custom classification terms list is a clinical term list, then the document is classified as a clinical document.

If the number of matching classification terms is below a matching threshold value, the matched terms are weighted differentially (e.g., four unique terms may be weighted with a factor of 0.3, five unique terms may be weighted with a factor of 0.6, and six unique terms may be weighted with a factor of 0.8), at operation 740. If the weighting score (e.g., sum of each unique term times a respective weighting factor) is above a classification threshold value, then the document is classified accordingly at operation 750. For example, if too few unique terms are identified, and the weighting score is below a classification threshold value, then the document will not be classified in the respective category.

Figure 4:
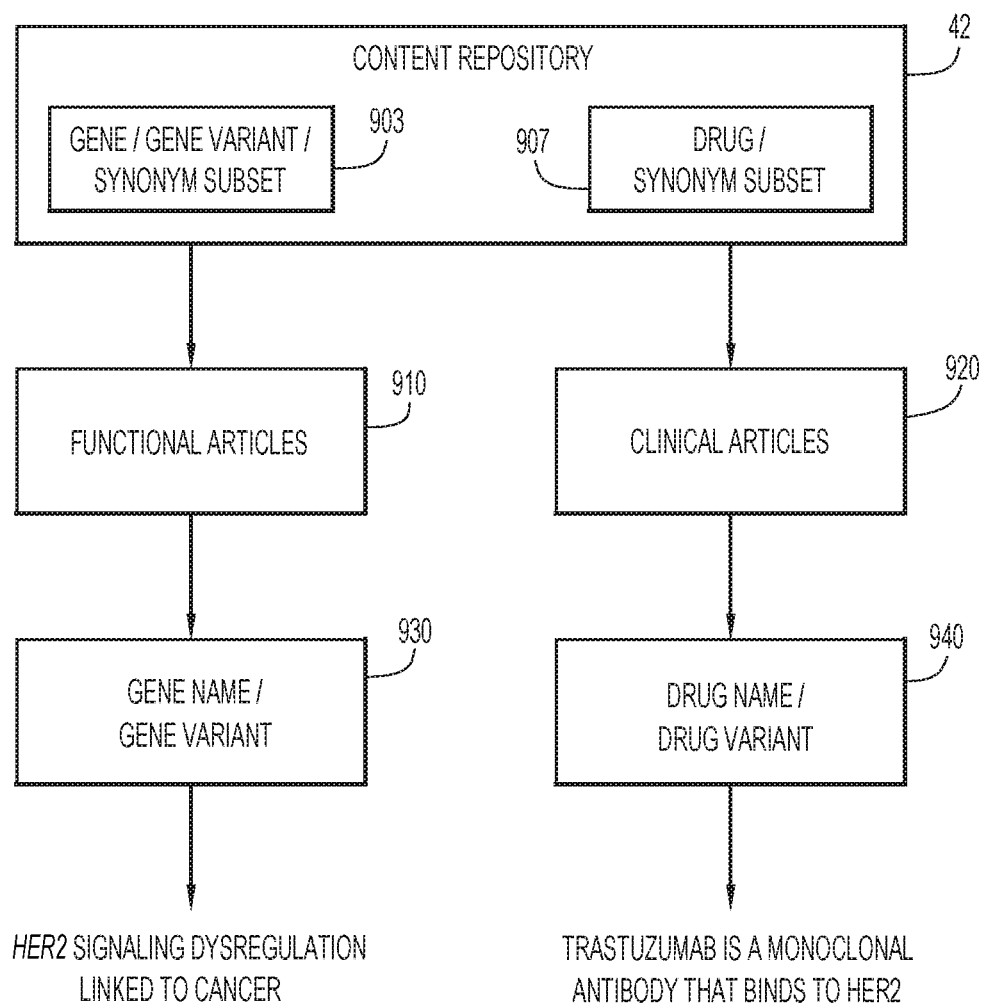
FIG. 4 is an example genomics and therapeutics application, according to embodiments of the present disclosure.

FIG. 4 provides an example of the document filtration system identifying and classifying documents and documents within document subsets that provide evidence pertinent to genomic cancer medicines. A content repository 42 may be filtered to generate a gene subset 903 (including gene name synonyms and gene variant name synonyms) and a drug subset 907 (including drug name synonyms), which may be respectively searched for functional articles 910 and clinical articles 920. The functional articles may be searched for particular gene or gene variant names 930 (or synonyms thereof) to return documents that link genes or gene variants (or other entities including synonyms thereof) to function (e.g., HER2 signaling dysregulation and amplification linked to cancer). The clinical articles may be searched for particular drug names 940 (or synonyms thereof) to return documents referencing drugs to treat a disease (e.g., a monoclonal antibody to bind to HER2). Thus, the present techniques provide a way to access relationships between documents, in a customized specific manner.

Figure 5:
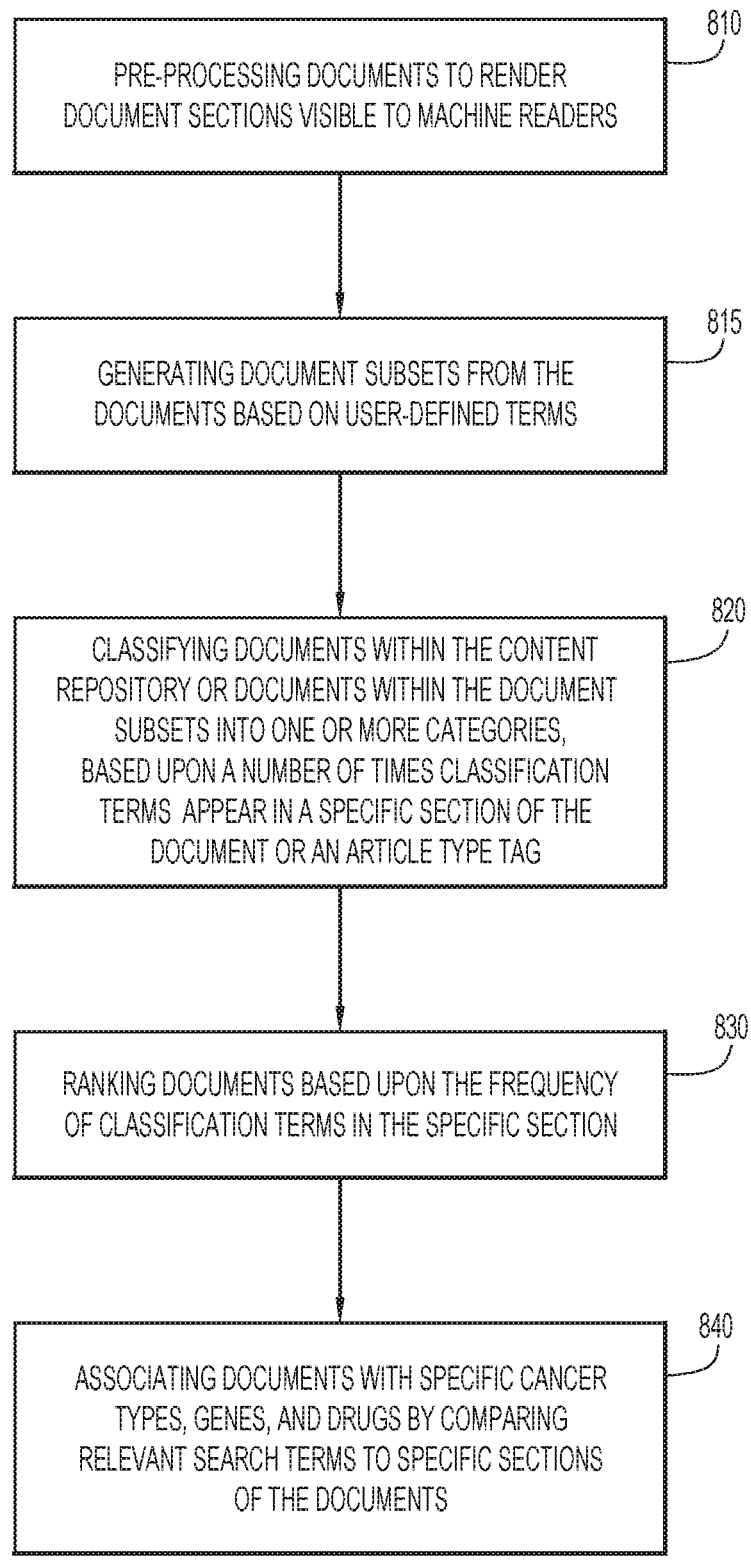
FIG. 5 is a high level flow diagram of the document filtration system, according to embodiments of the present disclosure.

FIG. 5 shows a flow chart of example operations. At operation 810, documents are pre-processed to render document sections visible to machine readers. At operation 815, document subsets are generated based on user-defined terms. For example, a list of genes (including gene name synonyms and gene variant name synonyms) may be used to filter a population of documents to generate a gene subset and a list of drugs (including drug name synonyms) may be used to filter a population of documents to generate a drug subset. At operation 820, documents are classified within the content repository into one or more categories (e.g., functional, clinical, case reports, review articles, or meetings and proceedings abstracts), based upon a number of times classification terms appear in a specific section of the document or an article type tag. At operation 830, documents are ranked based upon the frequency of classification terms in the specified section. At operation 840, documents are associated with specific diseases, genes, gene synonyms, gene variants, gene variant synonyms drugs, drug name synonyms, cancer-types and cancer-type name synonyms by comparing relevant search terms to specific sections of the documents. In some aspects, diseases may include a type of cancer such as breast, lung, pancreatic, ovarian, prostate, etc. In some aspects, relevant search terms may be provided, e.g., by a subject matter expert, wherein the search terms comprise genes, gene synonyms, gene variants, gene variant synonyms, drugs, drug synonyms, diseases, disease synonyms or cancer-types and cancer-type name synonyms.

Present techniques provide a variety of advantages over existing approaches. For example, the present system classifies and provides content from licensed documents immediately available to the user. The system may be fully customized to allow the user to choose what type of information to target (e.g., functional documents, clinical documents, etc. in combination with one or more genes, gene synonyms, gene variants, gene variant synonyms, targeted drugs, drug synonyms and cancer-types and cancer-type synonyms, etc.). To obtain different content, a user may change the custom classification terms lists or generate a new custom classification terms list to obtain targeted information. In some aspects, the terminology used for classification may be curated by experts in the field and may include gene names, gene synonym names, gene variant names, gene variant synonym names, gene targeted drug names, gene targeted drug synonym names, cancer-type names and cancer-type synonym names. Further, the results may be optionally ranked accordingly to relevancy of documents. For example, functional articles may be ranked based on the frequency of functional classifier terms in the materials and methods section of the article, while clinical articles may be ranked based on the frequency of clinical functional classifier terms in the abstract section of the article. By classifying the documents or document subsets based on a frequency of custom classification terms in a document, relevant content may be delivered to a user. Patients may be matched with specific functional mutations (e.g., genomic mutations that cause cancer, resistance mutations, etc.) with optimal clinical treatment for those factors. Present techniques also offer enhanced searching and new capabilities as a user can access particular types of content. In particular, users can access strictly functional articles or strictly clinical articles.

Figure 6:
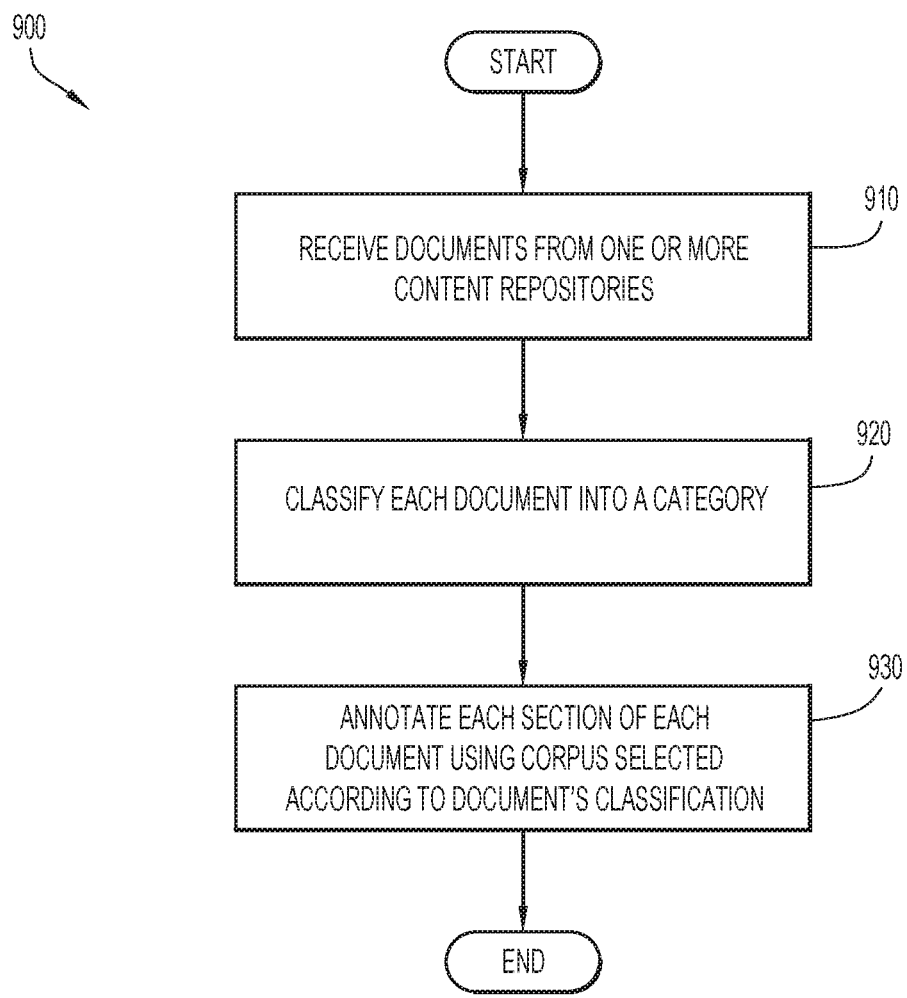
FIG. 6 is a flow chart depicting a method of annotating documents in accordance with an embodiment of the present invention.

FIG. 6 is a flow chart depicting a method 900 of annotating documents in accordance with an embodiment of the present invention.

The abstract sections of documents that are pre-classified as either functional or clinical studies are received from one or more content repositories at operation 910. Annotator module 76 may retrieve a title section and an abstract section of pre-classified functional or clinical documents.

Each document is classified into a functional category or a clinical category at operation 920. Annotator module 76 may classify a document as functional or clinical depending on whether the document contains functional information or clinical information. Functional information provides evidence relating to a gene's and/or gene variant's function, and clinical information provides evidence regarding a patient's response to treatment with a targeted therapy (e.g., in clinical studies). A natural language processing model may be used to annotate the text of abstracts to target clinically-relevant information. For instance, clinical study abstracts may often reference terms associated with biomarkers when a study has found that a particular genomic alteration confers resistance to a cancer therapy (e.g., a drug resistance biomarker), when a study predicts an increased risk of developing cancer (e.g., a predisposing biomarker), and the like.

Figure 7:
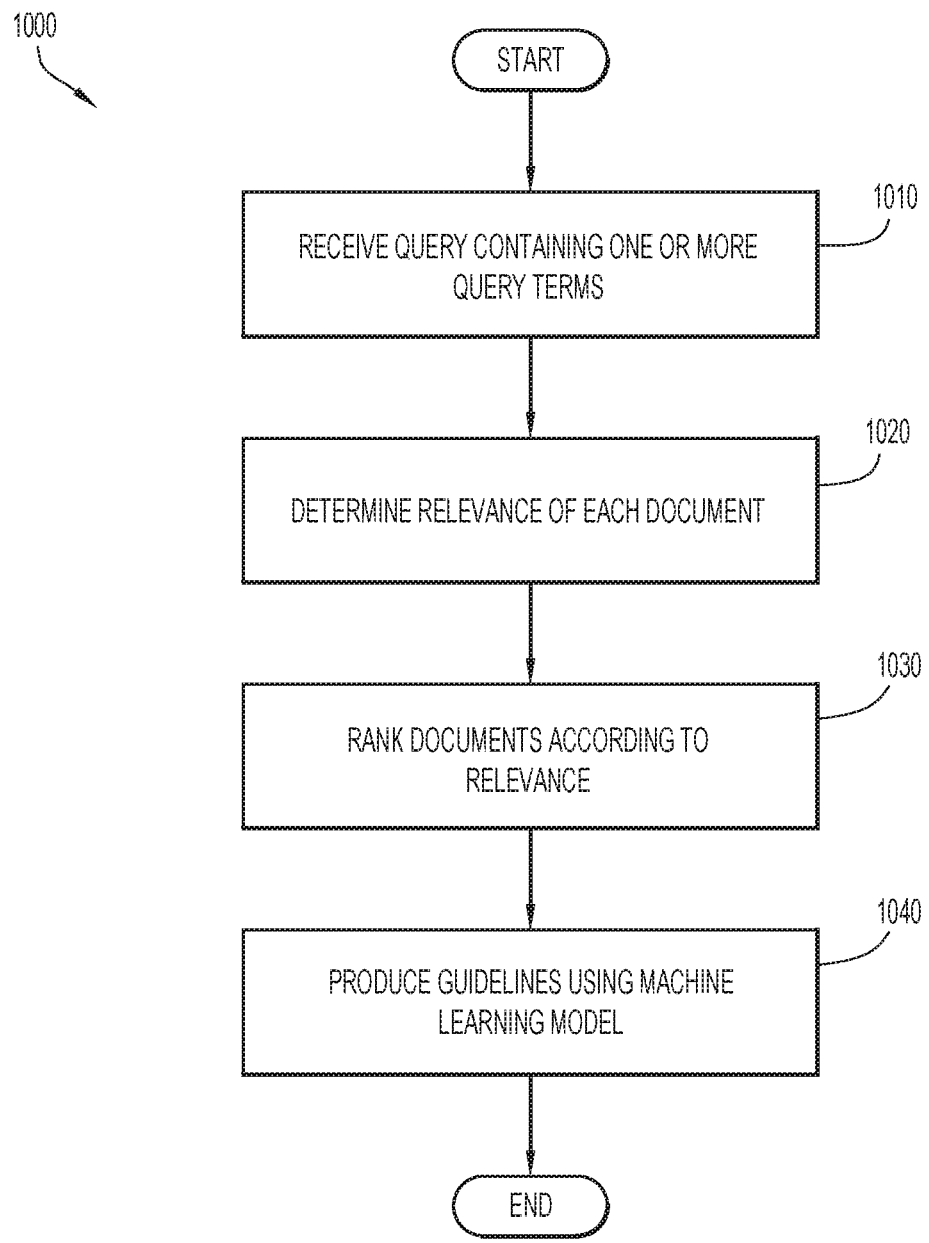
FIG. 7 is a flow chart depicting a method of processing documents in a content repository in accordance with an embodiment of the present invention.

FIG. 7 is a flow chart depicting a method 1000 of processing documents in a content repository in accordance with an embodiment of the present invention.

In some embodiments, query processing module 77 employs conventional or other machine learning techniques to generate a priority score for documents. Machine learning may be used to identify documents that may contain evidence of relationships between two or more query terms; documents that contain such evidence may receive higher priority scores. For example, a machine learning model may extract concepts and relationships from a document to determine that the document discusses two or more query terms in a manner that indicates a degree of relation to each other. This document may receive a higher priority score than another document that, while including the same two or more query terms, does not discuss the terms in a manner that indicates a relationship (e.g., there may be too many intervening words between the query terms, the query terms may appear in separate document sections from each other, etc.).

Documents are ranked according to their relevance at operation 1030. Once query processing module 77 assigns a priority score to each document, documents may be ranked according to their priority scores. Documents may be ranked in descending order of their priority scores in order to highlight the most relevant documents for a given query.

Guidelines are produced based on the ranked documents at operation 1040. Guideline module 78 may produce guidelines that include one or more diseases types that are each associated with data relating to precision medicine. For example, a guideline for precision medicine in oncology may indicate that the epidermal growth factor receptor (EGFR) exon 19 mutation is responsive to one or more specified targeted EGFR inhibitors.

In order to identify the data that is associated with the one or more disease types, the ranked documents from operation 1030 are utilized as a corpus to train a machine learning model to predict items, such as genes, biomarkers, and targeted therapies, that are related to a given disease types.

The guidelines may be organized according to disease type and disease subtype, which may each be associated with data extracted from documents that includes biomarkers, genes, gene variants, drugs, genomic data, proteomic data, metabolomics data, and any other data relating to clinical decision-making.

A natural language processing model may be used to annotate the text of abstracts to target clinically-relevant information. For instance, clinical study abstracts may often reference terms associated with biomarkers when a study has found that a particular genomic alteration confers resistance to a cancer therapy (e.g., a drug resistance biomarker), when a study predicts an increased risk of developing cancer (e.g., a predisposing biomarker), and the like. After documents are ranked based on the number and types of annotations extracted from each document, text that is associated with any of five biomarker types (diagnostic biomarkers, prognostic biomarkers, predisposing biomarkers, drug resistance biomarkers, and biomarkers relating to predicted responses to therapies) is extracted from the documents that have been pre-classified as clinical documents or functional documents. Clinically-relevant information may be placed into predetermined and relevant categories, including clinical data, pre-clinical data, gene activity and signaling pathway data, a disease status category, and the like. The categorized information may then be used to produce genomic-based guidelines to support clinical decision-making.

In some embodiments, the guidelines present the data associated with disease types in a particular hierarchy. First, data that is extracted from approved treatments may be presented. The treatments may be approved by one or more agencies, such as the United States Food and Drug Administration. The data extracted from approved treatments may include established, recommended procedures, and guideline module 78 may access one or more databases to ensure that the data is current. At a lower hierarchy level, the guidelines may include data relating to investigational biomarkers and therapies. As some biomarkers are associated with multiple investigational drugs, a machine learning model may be employed to predict the most potent investigational drug or drugs, and in the case of multiple investigational drugs, may rank them according to efficacy. The machine learning model may more highly rank an investigational drug when the drug is predicted to affect the least amount of off-target molecules, has the least unwanted side-effects, and the like.

References to the publications from which the data is extracted are included in the guidelines. The publications may be referenced according to a PubMed® identifier (PMID). In some embodiments, guideline module 78 retrieves a portion or all of the text of each document referenced in the guidelines. Guideline module 78 may transmit the referenced document (or portions thereof) to the computing device, such as client system 20, that provided the query, so that a user may view the referenced document (or portions thereof).

Figure 8:
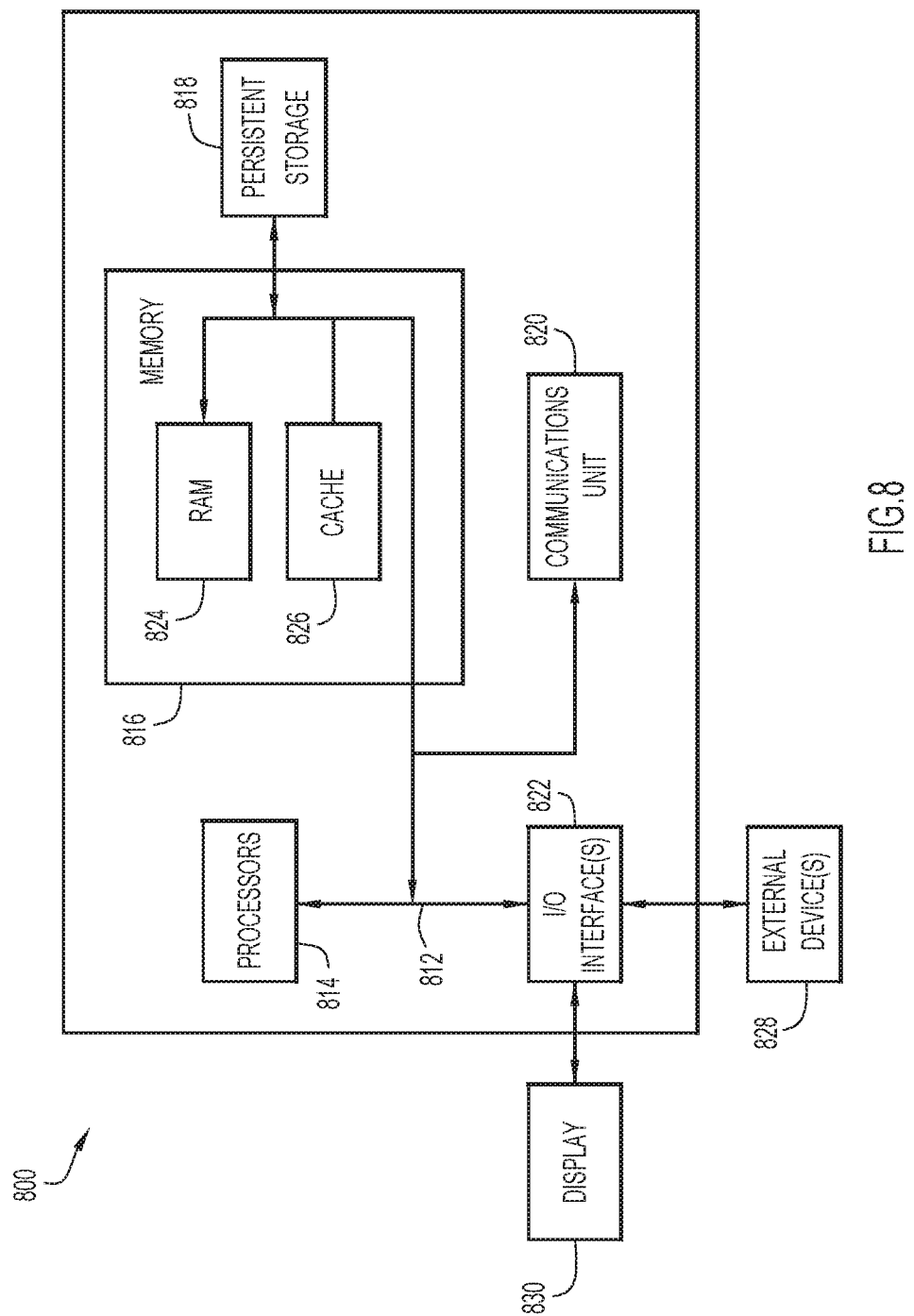
FIG. 8 is a block diagram depicting a computing device in accordance with an embodiment of the present invention.

FIG. 8 is a block diagram depicting components of a computer 800 suitable for executing the methods disclosed herein. Computer 800 may implement server systems 10, client systems 20, and/or database systems 40 in accordance with embodiments of the present invention. It should be appreciated that FIG. 8 provides only an illustration of one embodiment and does not imply any limitations with regard to the environments in which different embodiments may be implemented. Many modifications to the depicted environment may be made.

As depicted, the computer 800 includes communications fabric 812, which provides communications between computer processor(s) 814, memory 816, persistent storage 818, communications unit 820, and input/output (I/O) interface(s) 822. Communications fabric 812 can be implemented with any architecture designed for passing data and/or control information between processors (such as microprocessors, communications and network processors, etc.), system memory, peripheral devices, and any other hardware components within a system. For example, communications fabric 812 can be implemented with one or more buses.

Memory 816 and persistent storage 818 are computer readable storage media. In the depicted embodiment, memory 816 includes random access memory (RAM) 824 and cache memory 826. In general, memory 816 can include any suitable volatile or non-volatile computer readable storage media.

One or more programs may be stored in persistent storage 818 for execution by one or more of the respective computer processors 814 via one or more memories of memory 816. The persistent storage 818 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 818 may also be removable. For example, a removable hard drive may be used for persistent storage 818. Other examples include optical and magnetic disks, thumb drives, and smart cards that are inserted into a drive for transfer onto another computer readable storage medium that is also part of persistent storage 818.

Communications unit 820, in these examples, provides for communications with other data processing systems or devices. In these examples, communications unit 820 includes one or more network interface cards. Communications unit 820 may provide communications through the use of either or both physical and wireless communications links.

I/O interface(s) 822 allows for input and output of data with other devices that may be connected to computer 800. For example, I/O interface 822 may provide a connection to external devices 828 such as a keyboard, keypad, a touch screen, and/or some other suitable input device. External devices 828 can also include portable computer readable storage media such as, for example, thumb drives, portable optical or magnetic disks, and memory cards.

Software and data used to practice embodiments of the present invention can be stored on such portable computer readable storage media and can be loaded onto persistent storage 818 via I/O interface(s) 822. I/O interface(s) 822 may also connect to a display 830. Display 830 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Data relating to processing documents in a content repository to generate personalized treatment guidelines (e.g., document data and metadata, document annotation data, corpora data, query data, etc.) may be stored within any conventional or other data structures (e.g., files, arrays, lists, stacks, queues, records, etc.) and may be stored in any desired storage unit (e.g., database, data or other repositories, queue, etc.) The data transmitted between server 1005, content repository 42, and client device 1060 may include any desired format and arrangement, and may include any quantity of any types of fields of any size to store the data. The definition and data model for any datasets may indicate the overall structure in any desired fashion (e.g., computer-related languages, graphical representation, listing, etc.).

Data relating to processing documents in a content repository to generate personalized treatment guidelines (e.g., document data and metadata, document annotation data, corpora data, query data, etc.) may include any information provided to, or generated by, server systems 10, client systems 20, server 1005, content repository 42, and/or client device 1060. Data relating to processing documents in a content repository to generate personalized treatment guidelines may include any desired format and arrangement, and may include any quantity of any types of fields of any size to store any desired data. The data relating to processing documents in a content repository to generate personalized treatment guidelines may include any data collected about entities by any collection mechanism, any combination of collected information, and any information derived from analyzing collected information.

The present invention embodiments may employ any number of any type of user interface (e.g., Graphical User Interface (GUI), command-line, prompt, etc.) for obtaining or providing information (e.g., data relating to processing documents in a content repository to generate personalized treatment guidelines), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

It will be appreciated that the embodiments described above and illustrated in the drawings represent only a few of the many ways of processing documents in content repositories to generate personalized treatment guidelines.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., server software, communications software, document pre-processing module 71, document sectioning module 72, classifier term matching module 73, weighting/classification module 74, drug and gene subset module 75, annotator module 76, query processing module 77, guideline module 78, browser module 1070, etc.). These systems may include any types of monitors and input devices (e.g., keyboard, mouse, voice recognition, etc.) to enter and/or view information.

It is to be understood that the software (e.g., server software, communications software, document pre-processing module 71, document sectioning module 72, classifier term matching module 73, weighting/classification module 74, drug and gene subset module 75, annotator module 76, query processing module 77, guideline module 78, browser module 1070, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., server software, communications software, document pre-processing module 71, document sectioning module 72, classifier term matching module 73, weighting/classification module 74, drug and gene subset module 75, annotator module 76, query processing module 77, guideline module 78, browser module 1070, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., data relating to processing documents in a content repository to generate personalized treatment guidelines). The database system may be implemented by any number of any conventional or other databases, data stores or storage structures (e.g., files, databases, data structures, data or other repositories, etc.) to store information (e.g., data relating to processing documents in a content repository to generate personalized treatment guidelines). The database system may be included within or coupled to the server and/or client systems. The database systems and/or storage structures may be remote from or local to the computer or other processing systems, and may store any desired data (e.g., data relating to processing documents in a content repository to generate personalized treatment guidelines).

The present invention embodiments may employ any number of any type of user interface (e.g., Graphical User Interface (GUI), command-line, prompt, etc.) for obtaining or providing information (e.g., data relating to processing documents in a content repository to generate personalized treatment guidelines), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method of processing documents in a content repository, the method comprising:
   classifying each document of a plurality of documents into one of a functional category and a clinical category;
   annotating each document using one or more corpora to generate document annotations, wherein a first corpus is used to annotate documents in the functional category, and a second corpus is used to annotate documents in the clinical category;
   identifying documents satisfying one or more query terms by comparing each query term to the document annotations;
   ranking the identified documents based on a determined relevance, wherein the determined relevance of each document is determined using neural network-based machine learning; and
   producing guidelines based on the ranking of the identified documents.

2. The computer-implemented method of claim 1, wherein the query terms include one or more of a gene term, a gene variant term, a drug term, a resistance mutation term, and a disease term.

3. The computer-implemented method of claim 1, wherein ranking the identified documents comprises:
   calculating a priority score for each document, wherein the priority score is calculated according to a presence of one or more query terms in a document, and wherein each query term is weighted according to a section of the document in which the query term is located; and
   ranking the documents according to the priority score of each document.

4. The computer-implemented method of claim 1, wherein document annotations indicate a location and a frequency of a word or phrase in each document that matches a word or phrase in the one or more corpora.

5. The computer-implemented method of claim 1, wherein the guidelines comprise one or more disease types and corresponding data relating to precision medicine.

6. A computer system for processing documents in a content repository, the computer system comprising:
   one or more computer processors;
   one or more computer readable storage media;
   program instructions stored on the one or more computer readable storage media for execution by at least one of the one or more computer processors, the program instructions comprising instructions to:
   classify each document of a plurality of documents into one of a functional category and a clinical category;
   annotate each document using one or more corpora to generate document annotations, wherein a first corpus is used to annotate documents in the functional category, and a second corpus is used to annotate documents in the clinical category;
   identify documents satisfying one or more query terms by comparing each query term to the document annotations;
   rank the identified documents based on a determined relevance, wherein the determined relevance of each document is determined using neural network-based machine learning; and
   produce guidelines based on the ranking of the identified documents.

7. The computer system of claim 6, wherein the query terms include one or more of a gene term, a gene variant term, a drug term, a resistance mutation term, and a disease term.

8. The computer system of claim 6, wherein the instructions to rank the identified documents comprise instructions to:
   calculate a priority score for each document, wherein the priority score is calculated according to a presence of one or more query terms in a document, and wherein each query term is weighted according to a section of the document in which the query term is located; and rank the documents according to the priority score of each document.

9. The computer system of claim 6, wherein document annotations indicate a location and a frequency of a word or phrase in each document that matches a word or phrase in the one or more corpora.

10. The computer system of claim 6, wherein the guidelines comprise one or more disease types and corresponding data relating to precision medicine.

11. A computer program product for processing documents in a content repository, the computer program product comprising one or more computer readable storage media collectively having program instructions embodied therewith, the program instructions executable by a computer to cause the computer to:

classify each document of a plurality of documents into one of a functional category and a clinical category;

annotate each document using one or more corpora to generate document annotations, wherein a first corpus is used to annotate documents in the functional category, and a second corpus is used to annotate documents in the clinical category;

identify documents satisfying one or more query terms by comparing each query term to the document annotations;

rank the identified documents based on a determined relevance, wherein the determined relevance of each document is determined using neural network-based machine learning; and produce guidelines based on the ranking of the identified documents.

12. The computer program product of claim 11, wherein the query terms include one or more of a gene term, a gene variant term, a drug term, a resistance mutation term, and a disease term.

13. The computer program product of claim 11, wherein the instructions to rank the identified documents comprise instructions to:

calculate a priority score for each document, wherein the priority score is calculated according to a presence of one or more query terms in a document, and wherein each query term is weighted according to a section of the document in which the query term is located; and rank the documents according to the priority score of each document.

14. The computer program product of claim 11, wherein document annotations indicate a location and a frequency of a word or phrase in each document that matches a word or phrase in the one or more corpora.

15. The computer program product of claim 11, wherein the guidelines comprise one or more disease types and corresponding data relating to precision medicine.

* * * * *